(12) United States Patent
Audic et al.

(10) Patent No.: US 6,656,367 B1
(45) Date of Patent: Dec. 2, 2003

(54) METHOD FOR MANAGING URBAN WASTEWATER BASED ON INDICATIONS ON POLLUTANTS

(75) Inventors: Jean-Marc Audic, Conflans Ste Honorine (FR); Philippe Caulet, Bailly (FR); Rémy Gerard, Dijon (FR); Myriam Lefebure, Houilles (FR)

(73) Assignee: Ondeo Services, Nanterre (FR)

( * ) Notice: Subject to any disclaimer, the term of this patent is extended or adjusted under 35 U.S.C. 154(b) by 0 days.

(21) Appl. No.: 10/019,720

(22) PCT Filed: Jun. 29, 2000

(86) PCT No.: PCT/FR00/01812

§ 371 (c)(1),
(2), (4) Date: Apr. 25, 2002

(87) PCT Pub. No.: WO01/02306

PCT Pub. Date: Jan. 11, 2001

(30) Foreign Application Priority Data

Jul. 1, 1999 (FR) .............................................. 99 08493

(51) Int. Cl.$^7$ ................................................. C02F 1/00
(52) U.S. Cl. ........................ 210/739; 210/745; 210/746; 210/903; 210/906; 210/908

(58) Field of Search ................................. 210/739, 745, 210/746, 103, 903, 906, 908

(56) References Cited

U.S. PATENT DOCUMENTS 6,080,317 A * 6/2000 Wagner et al.
6,482,325 B1 * 11/2002 Corlett et al.

* cited by examiner

*Primary Examiner*—Betsey Morrison Hoey
(74) *Attorney, Agent, or Firm*—Connolly Bove Lodge & Hutz LLP

(57) ABSTRACT

A method for estimating incoming pollution loads during operation of a municipal wastewater treatment plant involves the step of continuously measuring the conductivity and turbidity of the raw water to be treated. The concentration of a pollutant in the raw water to be treated is estimated as a function of the measured conductivity and turbidity. The flow rate of the raw water to be treated is also continuously measured. The load of the pollutant in the raw water to be treated is estimated as a function of the estimated concentration of the pollutant and the measured flow rate. The estimated pollutant load allows adjustment of downstream treatment for eliminating the estimated total load of the pollutant.

5 Claims, 3 Drawing Sheets

METHOD FOR MANAGING URBAN WASTEWATER BASED ON INDICATIONS ON POLLUTANTS

FIELD OF THE INVENTION

The present invention relates in general to the running of municipal wastewater treatment plants on the basis of indications relating to pollution loads measured at the inlet of the treatment station, in the form of conductivity, turbidity and flow rate values: a practical illustration of this is given in the case of a treatment station using activated sludge for the physicochemical dephospatization of raw water simultaneously with purification by means of activated sludge, the objective of this invention being to define automated management rules for the addition of dephosphatizing reactants (ferric chloride) into the raw water proportional to the pollution load entering the station for purifying the said raw water.

BACKGROUND OF THE INVENTION

It is known that, to achieve this objective, it is necessary, on the one hand, to estimate, in line, the total phosphate load of the raw water to be treated and, on the other hand, to evaluate the yield of the dephosphatization reaction. In this way it is possible to determine the amount of dephosphatizing reactants to be added to the raw water, this amount having to be sufficient to remove the phosphorus so as to meet the imposed discharge standards, while still controlling the excess reactants so as to optimize the costs and avoid unjustified overproduction of additional sludge.

At the present time, this estimation is performed continuously by means of analysers, the investment costs of which are high and the running and maintenance of which are stringent.

The present invention is based on the discovery that, for municipal wastewater, any pollution load (whether carbon load, nitrogen load, phosphorus load, etc.) that has to be treated may be estimated from simple measurements of the flow rate conductivity and turbidity of the raw water.

The present proprietor has studied, for example, the relationship which exists between the total phosphorus load and:

the conductivity of the raw water to be treated;
the turbidity of the raw water; and
the flow rate of the raw water.

It should be pointed out that the invention is not limited to the treatment of raw water and that the use of load indicators is appropriate for controlling any purification phase in the treatment line.

For a given municipal wastewater, not containing more than 30% of its pollution flux originating from industrial discharges, it is accepted that the composition matrix of the water is relatively constant since the pollution source is essentially of domestic origin and comes from the users connected to the sewerage system.

DE-A-4 006 689 describes a method of managing water treatment plants based on measurements of the conductivity and turbidity of the water to be treated.

BRIEF DESCRIPTION OF THE INVENTION

Starting from the abovementioned observations and prior art, the present invention provides a method which consists, based on continuous measurements of the conductivity and turbidity of the raw water to be treated, in carrying out the following operations:

estimating the concentration of pollutants in the raw water, on the basis of the said conductivity and turbidity values thus measured;

continuously measuring the flow rate of the raw water to be treated;

calculating the load of pollutants in the raw water as a function of its flow rate; and determining downstream treatment actions to be taken to eliminate the estimated total load of the polluting component.

As will have been understood, the method forming the subject matter of the present invention aims to determine a pollutant concentration equivalent which is a function of the said pollution indicators, that is to say of the continuously measured conductivity and turbidity values. Measuring the flow rate of the raw water to be treated then makes it possible to determine the pollutant load from this estimated concentration.

According to the present invention, the polluting component to be eliminated may be an orthophosphate, a metaphosphate or a polyphosphate, or in general an organic or inorganic chemical compound containing phosphorus. This polluting component may also be a nitrate, or in general an organic or inorganic chemical compound containing nitrogen, or else an organic or inorganic chemical compound containing carbon.

According to the present invention, the relationship between the estimated concentration and the pollution indicators associates:

the conductivity with the dissolved pollution which, in the case of a pollution load consisting of phosphorus, is essentially composed of orthophosphates. Conductivity ranges are therefore associated with factors equivalent to the concentration of soluble phosphorus components;

the turbidity with the colloidal and particulate pollution, this pollution consisting of various components, including phosphorus, which relate to suspended matter. Turbidity ranges are therefore associated with factors equivalent to the concentration of insoluble phosphorus components.

DETAILED DESCRIPTION OF THE INVENTION

Figure 1:
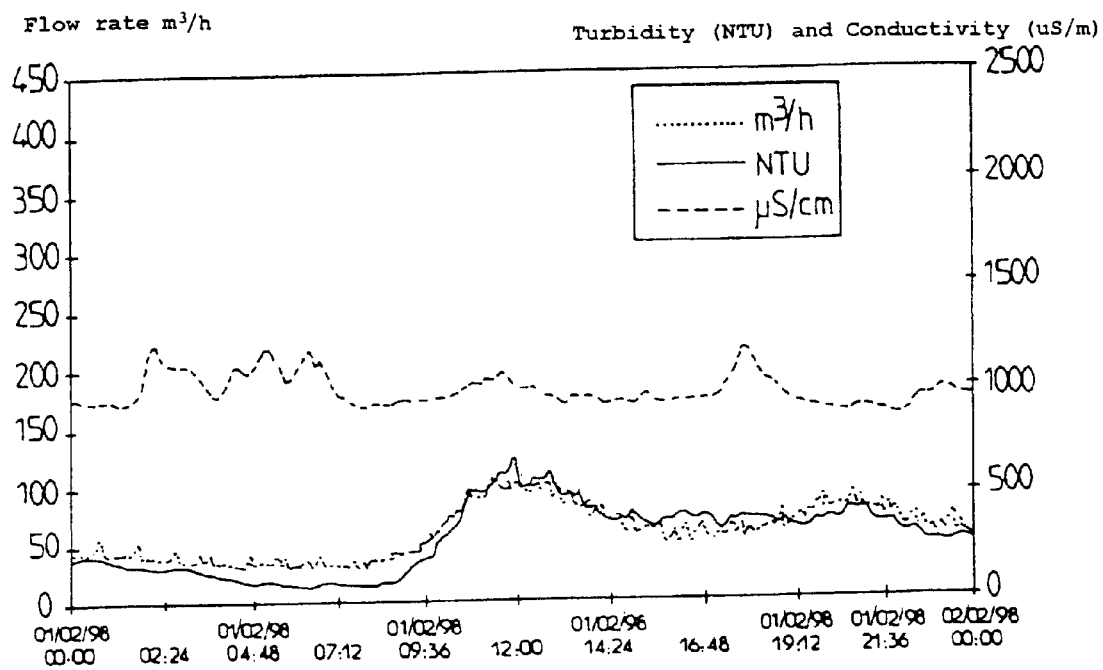
FIG. 1 is a plot illustrating variations, over time, of pollution indicators in dry whether.
Figure 2:
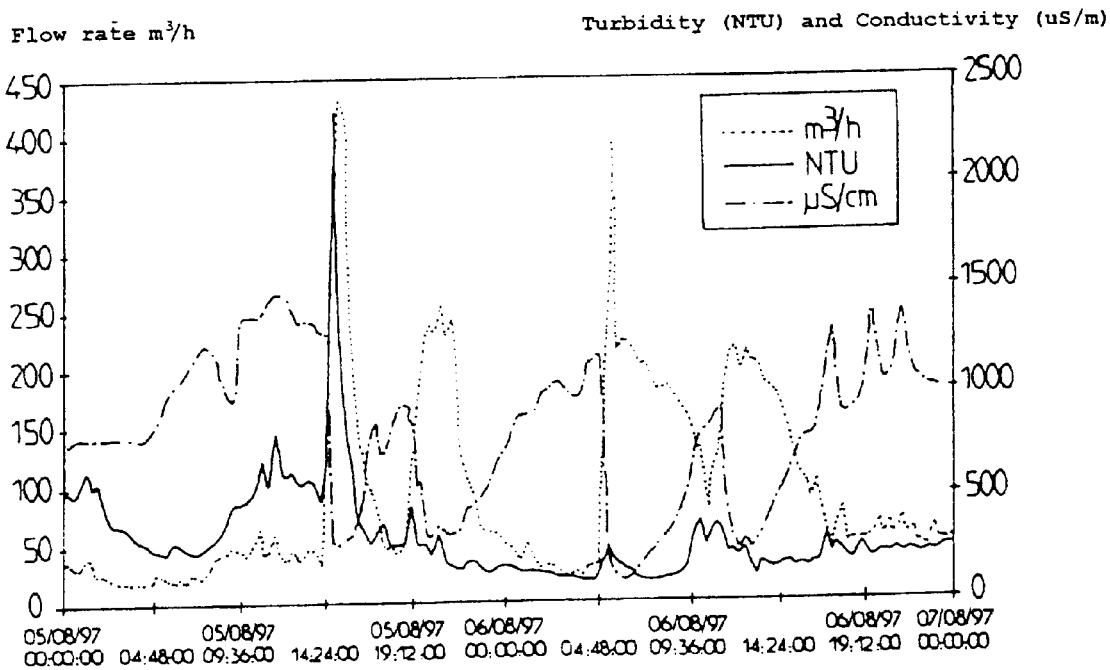
FIG. 2 is a plot illustrating variations, over time, of pollution indicators in wet whether.

FIGS. 1 and 2 of the appended drawings illustrate variations, over time, of the pollution indicators (conductivity and turbidity), the first one (FIG. 1) being typical of conditions in dry weather and the second one (FIG. 2) typical of conditions in rainy weather. The two parameters—conductivity and turbidity—vary differently when the domestic sewage is mixed with rainwater.

Dry Weather

The conductivity remains relatively constant during the daytime. In dry weather, the variation in turbidity follows that of the flow rate. The daily average concentrations of total phosphorus vary in this case between 10 and 15 mg/l.

Rainy Weather

FIG. 2 shows the variation in the conductivity and turbidity parameters during increases in flow rate arising from the rain phenomena.

In rainy weather, the increase in flow rate results systematically in a reduction in the conductivity. During the rain event, the reduction in conductivity is explained by a dilution of all of the solutes, and therefore by a dilution of the soluble phosphorus, quasi-systematically.

Right from the onset of the increase in flow rate, the turbidity behaves in two different ways:
- either the turbidity increases and reaches a high value, generally over a short period when the rain intensity is high, helping to convey stagnant deposits in the drains towards the inlet of the station (the example of the first day in FIG. 2). The increase in turbidity is a reflection of an increase in particulate pollution, and therefore in insoluble phosphorus;
- or the turbidity remains constant or even decreases slightly during the rain period, especially when the rain is not preceded by a relatively long dry period (the example of the second day in FIG. 2). A reduction in turbidity thus reflects a dilution of the insoluble components.

Based on these observations, two functions have been constructed so as to associate the measured values with the estimated concentrations of the desired components. It has been established that these functions must be calibrated on each site and tailored to each of the desired components. The calibration phase of these models consists, on the one hand, in continuously recording the three values of flow rate, conductivity and turbidity and, on the other hand, in carrying out, in parallel, campaigns to sample and analyse the wastewater.

Equivalent concentration values of soluble components are associated with conductivity ranges. For example, the concentration average of the samples is associated with the range of conductivity values usually encountered. The minimum concentration value of the samples is associated with the lowest conductivity range encountered. Conversely, the maximum concentration value of the samples is associated with the highest conductivity range encountered. The intermediate ranges are then determined by a linear relationship or by any other type of regression. The function is thus described in logic form with a correspondence between the conductivity range and the equivalent concentrations of the soluble component. In relation to the illustrations in FIGS. 1 and 2 pertaining to dry weather and to rainy weather, it is thus possible to give examples:

Function 1: if 1000 $\mu$S/cm<conductivity<1100 $\mu$S/cm,
then $[P]_{soluble}$=7 mg/l (dry weather);
if 200 $\mu$S/cm<conductivity<300 $\mu$S/cm,
then $[P]_{soluble}$=2 mg/l (rainy weather).

Function 2 is constructed in the same way by associating the equivalent concentration values of insoluble components with turbidity ranges.

Having carried out this learning phase, the continuous measurements can be used for implementing the method. To obtain an estimate of the pollution loads necessary for managing the methods, a total concentration is obtained by adding the complementary concentrations of soluble and insoluble components. This estimated concentration is multiplied by the flow rate so as to obtain an equivalent load.

The various steps of the method forming the subject matter of the present invention are therefore the following:

A) determination of the total concentration of a polluting component E, estimated complementarily as a function of the two physical pollution indicators (the conductivity and the turbidity):
concentration of the polluting component in soluble form as a function of the predetermined conductivity ranges, $[E]_{soluble}$=function$_1$ (conductivity)
concentration of the polluting component in insoluble form as a function of the predetermined turbidity ranges, $[E]_{insoluble}$=function$_2$ (turbidity)
estimated total concentration of the polluting component, $[E]_{total}$=$[E]_{soluble}$+$[E]_{insoluble}$;

B) determination of the total load of the polluting component (E) resulting from estimating the estimated total concentration of the component (E) and of the continuously measured flow rates:

Load $E_{total(estimated)}$=($[E]_{soluble}$+$[E]_{insoluble}$)×$Q_{inlet}$;

C) determination of the downstream treatment actions to be taken to eliminate the estimated total load of the polluting component E from the results obtained during the preliminary calibration of each plant (dosage of reactants, hourly aeration volume, aerobic/anoxic operation time, etc.).

In the example of how the invention is implemented in relation to phosphorus loads, the various steps of the method forming the subject matter of the invention are therefore the following:

A) determination of the total phosphorus concentration, estimated complementarily as a function of the two pollution indicators (conductivity and turbidity):
soluble phosphorus concentration as a function of the conductivity ranges: $[P]_{soluble}$=function 1 (conductivity)
insoluble phosphorus concentration as a function of the turbidity ranges: $[P]_{insoluble}$=function 2 (turbidity)
estimated total phosphorus concentration: $[P]_{total}$=$[P]_{soluble}$+$[P]_{insoluble}$;

B) determination of the estimated total phosphorus load, obtained from the estimate of the total phosphorus concentrations and the continuously measured flow rates:

Load $[P]_{total,estimate}$=($[P]_{soluble}$+$[P]_{insoluble}$)×$Q_{inlet}$;

C) determination of the amount of dephosphatizing reactants needed to eliminate the estimated total phosphorus load.

Figure 3:
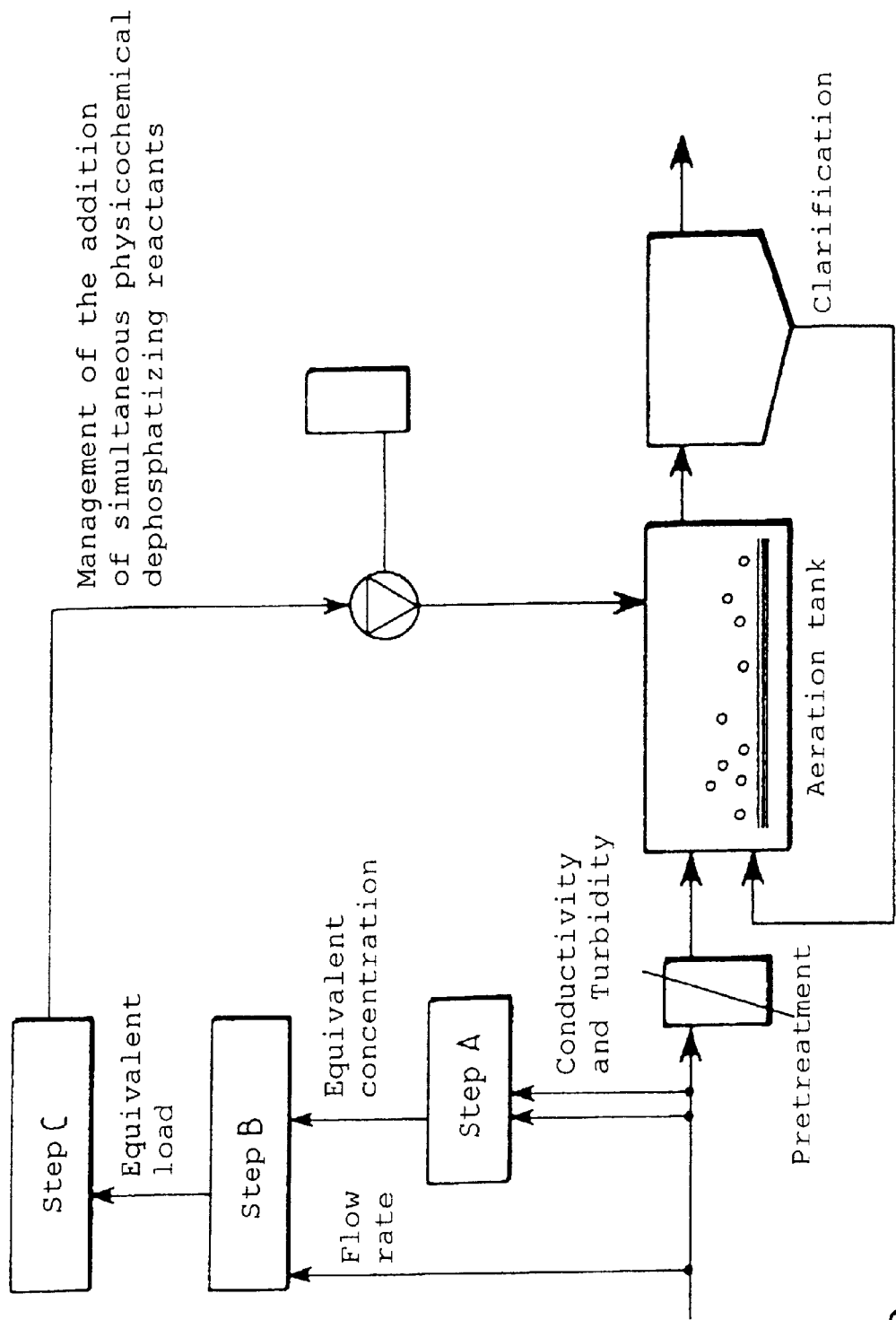
FIG. 3 is a block diagram illustrating the method of the present invention.

FIG. 3 of the appended drawings is a management diagram illustrating the method of the invention applied to simultaneous physicochemical dephosphatization.

Figure 4:
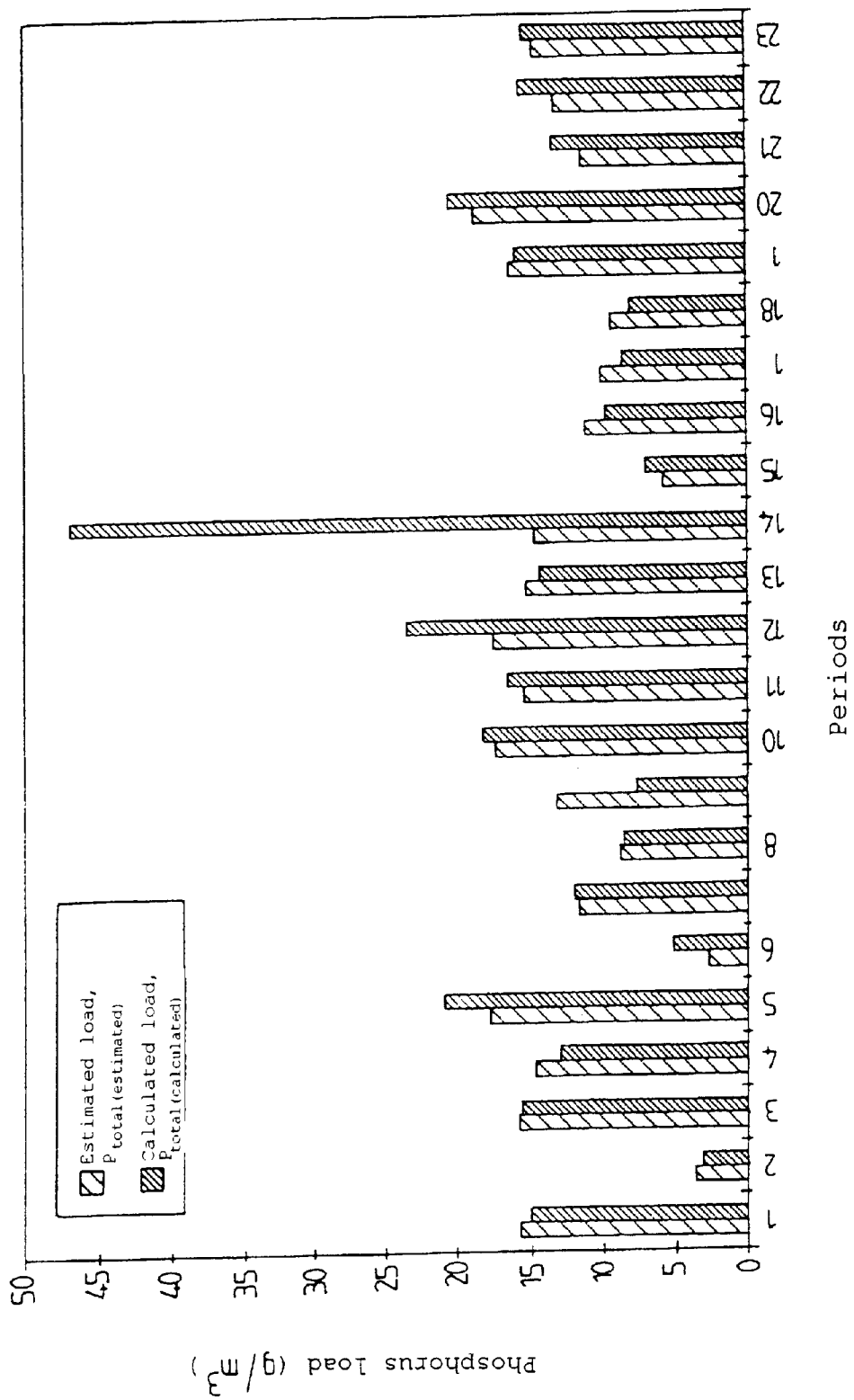
FIG. 4 is a plot of estimated load versus calculated load during various operational periods.

The present proprietor has made a comparison between the values obtained for the estimated total phosphorus load and for the calculated total phosphorus load over the periods in question. FIG. 4 of the appended drawings is a diagram illustrating this comparison.

Examination of this diagram shows that in most cases the estimated loads differ by less than 20% from the calculated loads. This demonstrates that the method forming the subject matter of the present invention allows the daily phosphorus loads of raw water to be effectively and reliably evaluated from the continuous measurements of the pollution indicators—conductivity and turbidity—and from the flow rate measurement.

Next, the amount of additions of dephosphatizing reactants (ferric chloride) needed to eliminate the estimated total phosphorus load is determined. In this way, automatic management of the additions of dephosphatizing reactants as a function of the three parameters—flow rate, conductivity and turbidity—is achieved without the need for continuous use of sophisticated equipment of the analyser type, since the equipment used by the method forming the subject matter of the invention is of quite conventional nature:

- the conductivity of the raw water is measured by electromagnetic induction using a conventional conductimeter;
- the turbidity is measured using a turbidity meter probe; and
- the flow rate is measured using a flow meter.

It will of course be understood that the present invention is not limited to the methods of implementation described and/or mentioned above; rather it encompasses all variants thereof.

What is claimed is:

1. A method of estimating incoming pollution loads during operation of a municipal wastewater treatment plant comprising the steps:

continuously measuring the conductivity of the raw water to be treated;

continuously measuring the turbidity of the raw water to be treated;

estimating the concentration of a pollutant in the raw water to be treated as a function of the measured conductivity and turbidity;

continuously measuring the flow rate of the raw water to be treated;

estimating the load of the pollutant in the raw water to be treated as a function of the estimated concentration of the pollutant and the measured flow rate; and subjecting the raw water to adjustable downstream treatment for eliminating the estimated total load of the pollutant.

2. The method according to claim 1, further comprising the following steps:

estimating the concentration of the pollutant in soluble form as a function of a predetermined conductivity range;

estimating the concentration of the pollutant in insoluble form as a function of a predetermined turbidity range;

estimating the total concentration of the pollutant as a function of the estimated soluble and insoluble concentrations; and estimating the total estimated load of the pollutant as a function of the estimated total concentration multiplied by the measured flow rate.

3. The method according to claim 1 wherein the pollutant to be eliminated is chosen from the group of organic or inorganic chemical compound containing phosphorus, including an orthophosphate, metaphosphate, or polyphosphate.

4. The method according to claim 1 wherein the pollutant to be eliminated is chosen from the group of organic or inorganic chemical nitrate compounds containing nitrogen.

5. The method according to claim 1 wherein the pollutant to be eliminated is chosen from the group of organic or inorganic chemical compounds containing carbon.

* * * * *

UNITED STATES PATENT AND TRADEMARK OFFICE
CERTIFICATE OF CORRECTION

PATENT NO.    : 6,656,367 B1
DATED         : December 2, 2003
INVENTOR(S)   : Jean-Marc Audic et al.

It is certified that error appears in the above-identified patent and that said Letters Patent is hereby corrected as shown below:

<u>Title page,</u>
Item [75], Inventors name should be changed from "Lefebure" to -- Lefebvre --.

Signed and Sealed this

Eleventh Day of May, 2004

JON W. DUDAS
*Acting Director of the United States Patent and Trademark Office*